United States Patent [19]

Feldman et al.

[11] Patent Number: 5,352,812

[45] Date of Patent: Oct. 4, 1994

[54] METATHESIS OF ACYCLIC OLEFINS USING AN IRIDIUM/SILVER CATALYST COMPOSITION

[75] Inventors: Jerald Feldman, Hockessin, Del.; Marcia B. France, Pasadena, Calif.

[73] Assignee: E. I. Du Pont de Nemours and Company, Wilmington, Del.

[21] Appl. No.: 88,712

[22] Filed: Jul. 8, 1993

[51] Int. Cl.$^5$ ................................. C11C 3/00
[52] U.S. Cl. .................... 554/163; 554/124; 560/247; 585/643; 585/708; 570/257; 568/69; 568/671
[58] Field of Search ............... 554/124, 163; 560/247; 585/643, 708; 568/69, 671; 570/257

[56] References Cited

U.S. PATENT DOCUMENTS 3,721,718  3/1973  Hughes et al. ............... 260/683 D
4,496,758  1/1985  Blewett et al. ............... 560/112
4,545,941  10/1985  Rosenburg .................. 260/410.7
4,654,462  3/1987  Basset et al. ................ 585/646
4,943,396  7/1990  Johnson ..................... 260/405.5

OTHER PUBLICATIONS

L. Porri et al., *Die Makro. Chem.* 175:3097–3115 (1974).
L. Porri et al., *Die Makro. Chem.* 176:3121–3125 (1975).
J. C. Mol, *J. Molecular Catalysis*, 65:145–162 (1991).
K. J. Ivin, "Olefin Metathesis", Chapter 8, Academic Press (1983).
R. Rossi et al., *Tetra. Lett.* 11:879–882 (1974).
F. Bianchi et al., *J. Org. Chem.* 202:99–105 (1980).

*Primary Examiner*—José G. Dees
*Assistant Examiner*—Deborah D. Carr

[57] ABSTRACT

The metathesis of functionalized and unfunctionalized acyclic olefins using catalyst compositions containing iridium and silver in a molar ration of 3 to 1.

8 Claims, 1 Drawing Sheet

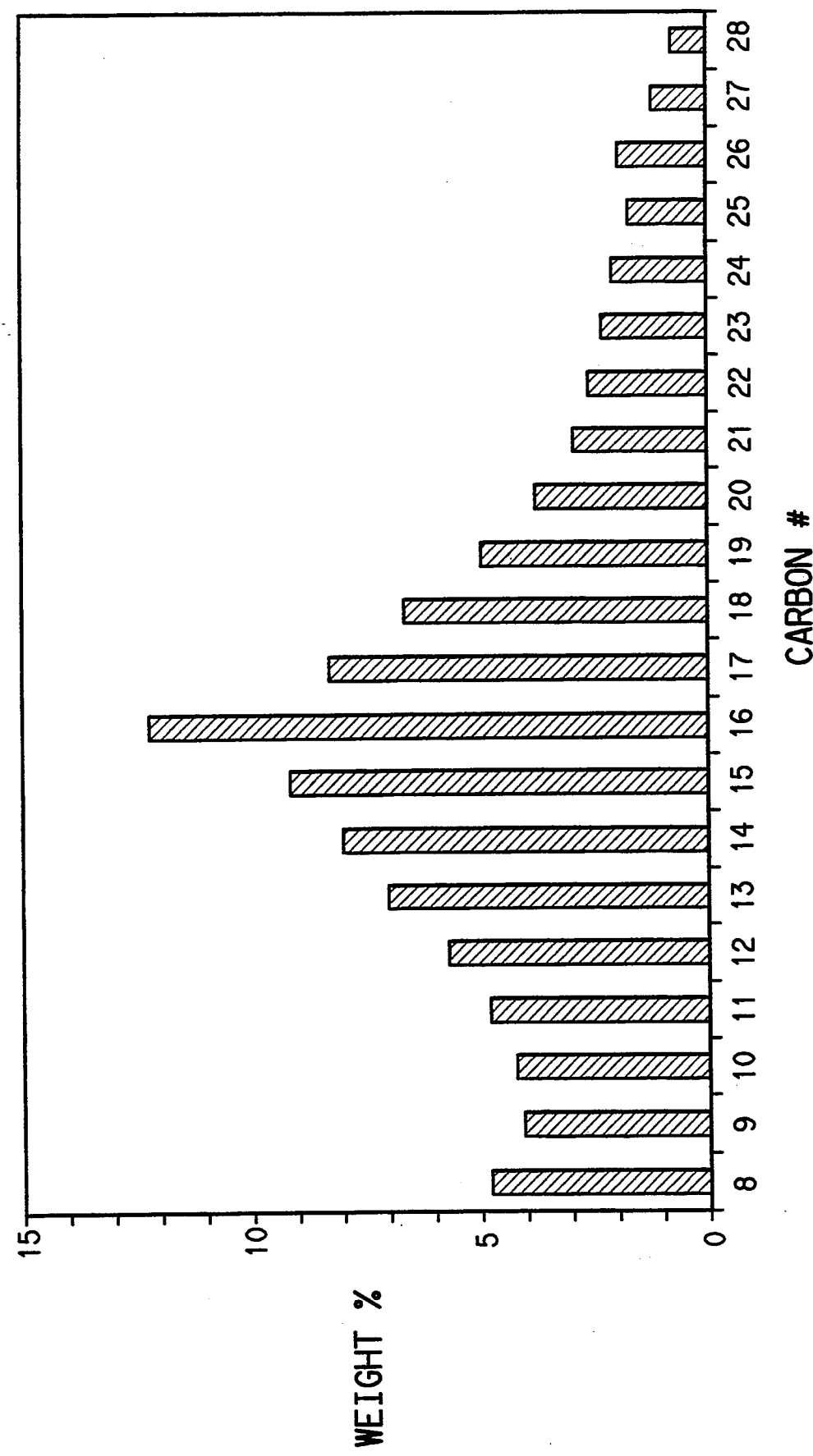

METATHESIS OF ACYCLIC OLEFINS USING AN IRIDIUM/SILVER CATALYST COMPOSITION

FIELD OF THE INVENTION

This invention relates to iridium catalyst compositions effective for the metathesis, with and without significant isomerization, of unfunctionalized and functionalized acyclic olefins.

BACKGROUND OF THE INVENTION

Catalysts which can isomerize and metathesize olefins are of great commercial importance, since, among other utilities, this reaction makes possible the production of olefins in desirable molecular weight ranges from olefins in undesirable molecular weight ranges.

Unfunctionalized olefin isomerization/metathesis is practiced commercially and is traditionally carried out in two steps (G. W. Parshall and S. D. Ittel Homogeneous Catalysis, Second Ed., Wiley, New York, 1992, Chapter 4.3). The present invention carries out the same chemistry in one step. Catalysts which can isomerize/metathesize functionalized olefins are also of potential commercial importance, since they make possible the synthesis of chemical feedstocks from highly functionalized biomass.

Much is known about ring opening metathesis polymerization of cyclic olefins catalyzed by iridium complexes. These are summarized in the book K. J. Ivin *Olefin Metathesis*, Academic Press, London, 1983, Chapter 2.6.3. However, there are very few references in the literature to acyclic olefin metathesis catalyzed by iridium. Porri et al., *Die Makromolekulare Chemie* 1974, 175, 3097, and Porri et al., *Die Makromolekulare Chemie* 1975, 176, 3121, describe a catalyst system [Ir(COE)$_2$Cl]$_2$+AgO$_2$CCF$_3$+CF$_3$CO$_2$H effective for the ring-opening metathesis polymerization of cyclopentene, cycloheptene, and cyclooctene, and isomerization/metathesis of 1-pentene. However, unlike Applicants' system, the Porri catalyst system: (1) requires the presence of CF$_3$CO$_2$H; (2) discloses a AgO$_2$CCF$_3$ to [Ir(COE)$_2$Cl]$_2$ ratio of 2 to 1; and (3) is formed in a two-step process. Additionally, in contrast to Applicants' disclosure, Porri's system is not disclosed for the metathesis of functionalized olefins. Further, in one embodiment of the present metathesis method, Applicants have observed that the extent of isomerization accompanying the metathesis reaction is greatly reduced due to pre-incubation of the catalyst components prior to addition of the starting olefin compound.

Much is known about metathesis of acyclic functionalized olefins using catalysts based on molybdenum, tungsten, rhenium, and in some instances ruthenium. These are summarized in J. C. Mol *J. Mol. Catal.* 1991, 65, 145 and K. J. Ivin *Olefin Metathesis*, Academic Press, London, 1983, Chapter 8. The disclosure of methyl oleate metathesis in the present invention is the first example of acyclic functionalized olefin metathesis catalyzed by an iridium based catalyst.

Other references which discuss related systems are Rossi et al., *Tetrahedron Lett.* 1974, 11, 879 and Bianchi et al., *J. Organomet. Chem.* 1980, 202, 99. Rhodium catalysts which can simultaneously isomerize and metathesize acyclic olefins are disclosed in Hughes et al., U.S. Pat. No. 3,721,718.

SUMMARY OF THE INVENTION

This invention provides a method for the metathesis of acyclic olefin compounds, comprising reacting a starting acyclic olefin compound containing n carbon atoms, in the presence of a catalyst composition comprising compounds of Formulas II and III

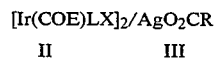

[Ir(COE)LX]$_2$/AgO$_2$CR
II          III wherein the molar ratio of compound III to compound II is at least 3 to 1; and
wherein X is Cl, Br, or I;
R is a C$_1$ to C$_{10}$ fluorinated hydrocarbyl;
COE is cyclooctene;
L is cyclooctene or P(C$_6$FS)$_3$; and
n is an integer between 3 and about 60;
to yield a mixture of acyclic olefin products containing 2 to 3n carbons.

Preferred embodiments of the method include wherein the components of the catalyst composition are preincubated prior to addition of the starting olefin; and wherein the molar ratio of compound III to compound II is at least 4 to 1.

This invention further provides a catalyst composition comprising compounds of Formulas II and III

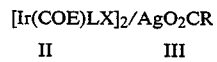

[Ir(COE)LX]$_2$/AgO$_2$CR
II          III wherein the molar ratio of compound III to compound II is at least 3 to 1; and
wherein X is Cl, Br, or I;
R is a C$_1$ to C$_{10}$ fluorinated hydrocarbyl;
COE is cyclooctene; and
L is cyclooctene or P (C$_6$F$_5$)$_3$.

Preferred embodiments of the composition include wherein X is Cl, R is CF$_3$; and wherein the molar ratio of compound III to compound II is at least 4 to 1.

BRIEF DESCRIPTION OF THE DRAWING

FIG. 1 demonstrates the metathesis/isomerization reaction products of the present invention on 1-hexadecene to yield olefin mixtures of C$_8$ to C$_{28}$.

DETAILED DESCRIPTION

Iridium catalysts have been discovered which catalyze isomerization and metathesis of acyclic olefins. Thus, given an acyclic olefin containing "n" carbon atoms, a range of acyclic olefins containing anywhere from 2 to approximately 3n carbon atoms are produced. The exact range obtained depends on the molecular weight of the starting olefin.

Significantly, these catalysts tolerate functional groups in the olefin; e.g., methyl oleate can be broken down into an extremely complex mixture of acyclic aliphatic olefins and acyclic unsaturated mono- and diesters by these catalysts.

Further, Applicants have found that when compounds of Formula II and 3 or more equivalents of compounds of Formula III are allowed to stir in contact with each other for several hours at room temperature prior to addition of the starting olefin, isomerization is suppressed and primarily metathesis products are observed. This is demonstrated as shown below using, for example, methyl oleate as the starting olefino.

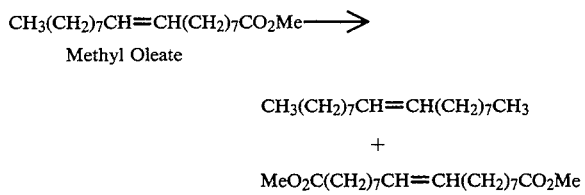

Methyl Oleate $$CH_3(CH_2)_7CH=CH(CH_2)_7CH_3$$
$$+$$
$$MeO_2C(CH_2)_7CH=CH(CH_2)_7CO_2Me$$

the catalyst of the present invention is prepared in situ by the addition of the silver salt of a fluorinated acid, $AgO_2CR$, to an iridium cyclooctene halide complex such as $[Ir(COE)_2Cl]_2$, the structure of which is shown below.

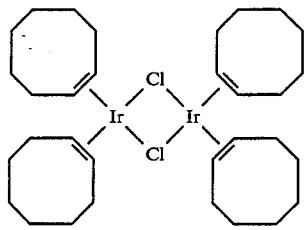

When two equivalents of $AgO_2CR$ are added to $[Ir(COE)_2Cl]_2$, the major products are silver chloride and $[Ir(COE)_2O_2CR]_2$. If two equivalents of $AgO_2CR$ are added to $[Ir(COE)_2Cl]_2$ in the presence of a linear olefin, the olefin undergoes double bond isomerization, but no metathesis of the resulting olefin mixture is observed. When more than two equivalents of $AgO_2CR$ are added to $[Ir(COE)_2Cl]_2$, the initial products are again silver chloride and $[Ir(COE)_2O_2CR]_2$, but the latter undergoes further reaction with the excess $AgO_2CR$ present to give silver metal and higher oxidation state iridium complexes active for olefin metathesis. Thus, when more than two equivalents of $AgO_2CR$ are added to $[Ir(COE)_2Cl]_2$ in the presence of an acyclic olefin containing n carbon atoms, the olefin undergoes double bond isomerization and the resulting mixture of olefins undergoes metathesis, resulting in a complex mixture of olefins containing between 2 and approximately 3n carbon atoms. The significant dual role of the silver salt in this chemistry (to precipitate silver chloride in the reaction with $[Ir(COE)_2Cl]_2$ and oxidize the resulting Ir(I) trifluoroaceate complex) does not appear to have been recognized by Porri et. al. (see, for example, F. Bianchi, M. C. Gallazzi, L. Porri, and P. Diversi *J. Organomet. Chem.* 1980, 202, 99).

Recognition of the dual role of the silver salt in this chemistry has made possible the following discovery: when a mixture of $[Ir(COE)LCl]_2$ and 4 or more equivalents of $AgO_2CCF_3$ is allowed to stir for several hours at room temperature prior to addition of the acyclic olefin, isomerization is suppressed and primarily the metathesis products of the starting acyclic olefin are formed.

In principle, any iridium halide complex of the formula $[Ir(COE)LX]_2$ which will react with 2 equivalents $AgO_2CR$ to give AgX and $[Ir(COE)LO_2CR]_2$ as products, is a viable catalyst precursor. "X" can be Cl, Br, or I. R can be any fluorinated hydrocarbyl containing between 1 and about 10 carbon atoms; e.g., trifluoromethyl, pentafluoroethyl, or heptafluoropropyl. Preferred is $CF_3$.

The acyclic olefin undergoing isomerization/metathesis can contain anywhere from 3 to about 60 carbon atoms. The olefin can be functionalized; possible functional groups include esters, ethers, halogens, and sulfides.

The reaction can be carried out at temperatures between about 25° and 150° C., and pressures between 1 and 100 atmospheres (1 atm = $1.01 \times 10^5$ Pascals). Temperatures between 25° and 100° C., and pressures between and 10 atmospheres are preferred.

The reaction may be carried out in an organic solvent. Suitable solvents include benzene, toluene, methylene chloride, acetone, diethyl ether, and tetrahydrofuran. Preferred is an aromatic solvent such as benzene or toluene.

The catalyst system is somewhat air sensitive and the reactions are best carried out under an inert atmosphere, e.g. nitrogen or argon.

$[Ir(COE)_2Cl]_2$ is a known compound and can be readily synthesized by one skilled in this art, and for example, a procedure can be found in the following: J. L. Herde, J. C. Lambert, and C. V. Senoff *Inorganic Syntheses* 1974, 15, 18. $[(COE)_2IrCl]_2$ is also available commercially from Aldrich Chemical Co., Milwaukee, Wis., USA. The salts silver trifluoroacetate, silver pentafluoropropionate, and silver heptafluorobutyrate are also commercially available; for example, from the Aldrich Chemical Company.

The complex $\{Ir(COE)P(C_6F_5)_3Cl\}_2$ was prepared as follows. $[Ir(COE)_2Cl]_2$ (1.00 g, 1.12 mmol) and $P(C_6F_5)_3$ (1.19 g, 2.23 mmol) (Aldrich Chemical) were suspended in 30 mL of toluene under a nitrogen atmosphere. The reaction mixture was stirred overnight at room temperature, during which time the reactants dissolved to give a clear orange-red solution. Volatiles were removed in vacuo to afford an orange-red foam. The crude product was recrystallized from toluene/petroleum ether at $-40°$ C. to afford $\{Ir(COE)P(C_6F_5)_3Cl\}_2$ as a yellow-orange powder (1.72 g, 89%).

EXAMPLE 1

This example demonstrates the metathesis/isomerization reaction of 1-hexadecene to give olefins containing between 4 and 28 carbon atoms, followed by hydrogenation of the product mixture to give alkanes as products.

Under nitrogen, silver trifluoroacetate (99 mg, 0.45 retool) and 1-hexadecene (488 mg, 2.18 mmol) were dissolved in 4.0 mL of toluene. To this solution was added $[Ir(COE)_2Cl]_2$ (78 mg, 0.087 mmol). The resulting heterogeneous, orange-red reaction mixture was stirred at room temperature for 24 h, during which time it became red-brown. An aliquot was withdrawn after 24 h, and analyzed by gas chromatography (GC): olefins containing between 4 and 28 carbon atoms each could be detected; hexadecene isomers accounted for approximately 10% of the olefin mixture at this time.

In order to better analyze the complex product mixture, it was hydrogenated to a mixture of alkanes as follows. Under nitrogen, the remaining reaction mixture from above, 4 mL of methanol, and 0.5 g 0.5% Pd/C were loaded into a 10 mL Hastelloy ™ C shaker tube. The tube was pressurized with 100 psi hydrogen gas (1 psi = $6.89 \times 10^3$ Pascal), and heated at 85° C. for 18 h. The product mixture was analyzed using a gas chromatograph equipped with a flame ionization detector. Linear alkanes (confirmed by mass spectroscopy)

containing between 7 and 28 carbon atoms could be detected. Their relative weight percent is indicated by FIG. 1.

EXAMPLE 2

This example demonstrates metathesis/isomerization of 1-dodecene. Under nitrogen, silver trifluoroacetate (37 mg, 0.17 mmol) and 1-dodecene (118 mg, 0.700 mmol), were dissolved in 1 mL of toluene. To this was added Ir(COE)$_2$Cl]$_2$ (25 mg, 0.028 mmol). The resulting heterogeneous, bright orange reaction mixture was stirred at room temperature for 16 h, and then analyzed by GC. Olefins containing between 4 and 26 carbon atoms could be detected; dodecene isomers accounted for approximately 15% of the olefin mixture.

EXAMPLE 3

This example demonstrates metathesis/isomerization of 1-octene. Under nitrogen, silver trifluoroacetate (25 mg, 0.112 mmol) and 1-octene (78 mg, 0.700 mmol) were dissolved in 1 mL of toluene. To this was added [Ir(COE)$_2$Cl]$_2$ (25 mg, 0.028 mmol). The resulting heterogeneous, bright orange reaction mixture was stirred at room temperature for 14 h, and then analyzed by GC. Olefins containing between 4 and 22 carbon atoms could be detected; octene isomers accounted for approximately 10% of the olefin mixture.

EXAMPLE 4

This example demonstrates metathesis/isomerization of 1-octadecene. Under nitrogen, silver trifluoroacetate (49 mg, 0.224 mmol) and 1-octadecene (353 mg, 1.40 mmol) were dissolved in 2 mL of toluene. To this was added [Ir(COE)$_2$Cl]$_2$ (50 mg, 0.056 mmol). The resulting heterogeneous, bright orange reaction mixture was stirred at room temperature for 8.5 h, and then analyzed by GC. Olefins containing between 4 and 32 carbon atoms could be detected; octadecene isomers accounted for approximately 10% of the olefin mixture.

EXAMPLE 5

This example demonstrates the metathesis/isomerization reaction of 1-hexadecene, using silver pentafluoropropionate in place of silver trifluoroacetate (cf. example 1). Under nitrogen, silver pentafluoropropionate (45 mg, 0.17 mmol) and 1-hexadecene (156 mg, 0.698 mmol) were dissolved in 1 mL of toluene. To this solution was added [Ir(COE)$_2$Cl]$_2$ (25 mg, 0.028 mmol). The resulting heterogeneous, bright orange reaction mixture was stirred at room temperature for 17 h, at which time it was analyzed by GC. Olefins containing between 4 and 28 carbon atoms could be detected; hexadecene isomers accounted for approximately 40% of the olefin mixture.

EXAMPLE 6

This example demonstrates the metathesis/isomerization reaction of 1-hexadecene, using silver heptafluorobutyrate in place of silver trifluoroacetate (cf. example 1). Under nitrogen, silver heptafluorobutyrate (54 mg, 0.17 mmol) and 1-hexadecene (125 mg, 0.557 mmol) were dissolved in 1 mL of toluene. To this solution was added [Ir(COE)$_2$Cl]$_2$ (25 mg, 0.028 mmol). The reaction mixture was stirred at room temperature for 4 days, and then analyzed by GC. Olefins containing between 4 and 28 carbon atoms could be detected; hexadecene isomers accounted for approximately 25% of the olefin mixture.

EXAMPLE 7

This example demonstrates the metathesis/isomerization reaction of methyl oleate to give unfunctionalized olefins, unsaturated monoesters, and unsaturated diesters over a wide range of molecular weights, followed by hydrogenation of the product mixture to give alkanes, saturated monoesters, and saturated diesters.

Under nitrogen, silver trifluoroacetate (50 mg, 0.23 mmol) and methyl oleate (326 mg, 1.10 mmol) were dissolved in 3.0 mL of toluene. To this solution was added [Ir(COE)$_2$Cl]$_2$ (40 mg, 0.045 mmol). The resulting heterogeneous, orange reaction mixture was stirred at 85° C. for 22 h, during which time it became redbrown. An aliquot was then taken from the reaction mixture and analyzed by GC: a complex mixture of unfunctionalized linear olefins, unsaturated linear monoesters, and unsaturated linear diesters over a wide range of molecular weights was present; methyl oleate and its isomers accounted for approximately 50% of the reaction mixture.

In order to better analyze the complex product mixture, it was hydrogenated to a mixture of alkanes, saturated monoesters, and saturated diesters as follows. Under nitrogen, the remaining reaction mixture from above, 4 mL of methanol, and 0.5 g 0.5% Pd/C were loaded into a 10 mL Hastelloy ™ C shaker tube. The tube was pressurized with 100 psi hydrogen gas, and heated at 85° C. for 18 h.

By analysis of the reaction mixture by GC/mass spectroscopy, linear alkanes containing between 9 and 26 carbon atoms, saturated linear methyl esters containing between 8 and 28 carbon atoms, and saturated linear dimethyl esters containing between 11 and 26 carbon atoms could be detected.

EXAMPLE 8

This example demonstrates the selective metathesis of methyl oleate to give 9-octadecene and MeO$_2$C(CH$_2$)$_7$CH=CH(CH$_2$)$_7$CO$_2$Me. Under nitrogen, [Ir(COE)$_2$Cl]$_2$ (25 mg, 0.028 mmol) and silver trifluoroacetate (37 rag, 0.167 mmol) were dissolved in 2.0 mL of toluene. The resulting heterogeneous, bright orange reaction mixture was stirred at room temperature for 45 h; during this time the reaction mixture became redbrown and a grey solid precipitated. Methyl oleate (83 rag, 0.28 mmol) was then added to the reaction mixture, which was stirred at room temperature for an additional 8 h. Analysis of the reaction mixture by GC indicated formation of the two metathesis products shown in the equation below as the major products. The molar ratio of unreacted methyl oleate to CH$_3$(CH$_2$)$_7$CH=CH(CH$_2$)$_7$CH$_3$ plus MeO$_2$C(CH$_2$)$_7$CH=CH(CH$_2$)$_7$CO$_2$Me was approximately 4 to 1.

Methyl Oleate

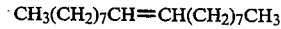
+
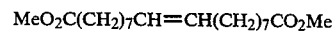

EXAMPLE 9

This example demonstrates the use of $\{Ir(COE)P(C_6F_5)_3Cl\}_2/AgO_2CCF_3$ as a catalyst for 1-hexadecene metathesis/isomerization. Silver trifluoroacetate (100 rag, 0.45 mmol) and 1-hexadecene (492 rag, 2.19 mmol) were dissolved in 4.0 mL of toluene. To this was added $\{Ir(COE)P(C_6F_5)_3Cl\}_2$ (152 mg, 0.087 mmol). The resulting heterogeneous, orange reaction mixture was stirred at room temperature. An aliquot was withdrawn after 23 h, and analyzed by gas chromatography (GC): olefins containing between 4 and 28 carbon atoms each could be detected; hexadecene isomers accounted for approximately 10% of the olefin mixture at this time.

EXAMPLE 10

This example demonstrates the use of methylene chloride as a solvent in the metathesis/isomerization reaction of 1-octadecene (cf. example 4). Under nitrogen, silver trifluoroacetate (49 mg, 0.224 mmol) and 1-octadecene (353 rag, 1.40 mmol) were dissolved in 2 mL of methylene chloride. To this was added $Ir(COE)_2Cl]_2$ (50 mg, 0.056 mmol). The resulting heterogeneous, bright orange reaction mixture was stirred at room temperature for 8 h, and then analyzed by GC. Olefins containing between 4 and 32 carbon atoms could be detected; octadecene isomers accounted for approximately 30% of the olefin mixture.

COMPARATIVE EXAMPLE 11

In this example, $[Ir(COE)_2Cl]_2/AgO_2CCF_3$ is used as a catalyst for 1-hexadecene metathesis/isomerization, and the molar ratio of $AgO_2CCF_3$ to $[Ir(COE)_2Cl]_2$ is 2 to 1. Under nitrogen, silver trifluoroacetate (12 mg, 0.056 mmol) and 1-hexadecene (157 rag, 0.700 mmol) were dissolved in 1 mL of toluene. To this solution was added $[Ir(COE)_2Cl]_2$ (25 mg, 0.028 mmol). The resulting red-purple solution was stirred at room temperature for 15 h, during which time it became a heterogeneous redbrown mixture. Analysis of the reaction mixture by GC showed extensive double bond isomerization, but only trace amounts of metathesis products; unreacted 1-hexadecene and its isomers comprised approximately 90% of the olefin mixture.

COMPARATIVE EXAMPLE 12

In this example, $[Ir(COE)_2Cl]_2/AgO_2CCF_3/CF_3CO_2H$ is used as a catalyst for 1-hexadecene metathesis/isomerization, and the molar ratio of $AgO_2CCF_3$ to $[Ir(COE)_2Cl]_2$ is 2 to 1. This example was run identically to Comparative Example 11, except trifluoroacetic acid (16 rag, 0.14 mmol) was added to the reaction mixture. Analysis of the reaction mixture by GC showed only trace amounts of metathesis/isomerization products; unreacted 1-hexadecene and its isomers comprised approximately 90% of the olefin mixture.

What is claimed is:

1. A method for the metathesis of acyclic olefin compounds, comprising
reacting a starting acyclic olefin compound containing n carbon atoms, in the presence of a catalyst composition comprising compounds of Formula II and III $$[Ir(COE)LX]_2 \quad AgO_2CR$$
$$\text{II} \qquad\qquad \text{III}$$

wherein the molar ratio of compound III to compound II is at least 3 to 1; and
wherein X is Cl, Br, or I;
R is a $C_1$ to $C_{10}$ fluorinated hydrocarbyl;
COE is cyclooctene;
L is cyclooctene or $P(C_6F_5)_3$; and
n is an integer between 3 and about 60;
to yield a mixture of acyclic olefin products containing 2 to 3n carbons.

2. The method of claim 1, wherein the starting acyclic olefin is substituted with one or more ester, ether, halogen, or sulfide groups.

3. The method of claim 1, wherein the catalyst compounds of Formula II and Formula III are stirred in contact with each other prior to the addition of the starting acyclic olefin.

4. The method of claim 2, wherein the starting acyclic olefin compound is a monounsaturated ester compound of Formula IV $$R^1CH=CH(CH_2)_mCO_2R^2$$
$$\text{IV}$$

wherein
$R^1$ is H or $CH_3(CH_2)_p$;
$R^2$ is $(CH_2)_qCH_3$;
m is an integer between 1 and about 15;
p is an integer between 0 and about 15; and
q is an integer between 0 and about 15;
to yield a mixture of acyclic olefins, monounsaturated esters and monounsaturated diesters containing between 2 and about 2(m+p+q) carbon atoms.

5. The method of claim 3, wherein the starting acyclic olefin is a monounsaturated ester compound of Formula IV $$R^1CH=CH(CH_2)_mCO_2R^2$$
$$\text{IV}$$

wherein
$R^1$ is H or $CH_3(CH_2)_p$; and
$R^2$ is $(CH_2)_qCH_3$;
m is an integer between 1 and about 15;
p is an integer between 0 and about 15; and
q is an integer between 0 and about 15;
and wherein the catalyst compounds of Formula II and Formula III are allowed to react with each other for at least 1 hour prior to the addition of compound IV, to yield product compounds of Formulas V and VI $$R^1CH=CHR^1 \quad R^2O_2C(CH_2)_mCH=CH(CH_2)_mCO_2R^2$$
$$\text{V} \qquad\qquad\qquad \text{VI}$$

wherein
$R^1$ $R^2$ and m are defined as above.

6. The method of claim 5, wherein the starting linear olefin compound is $CH_3(CH_2)_7CH=CH(CH_2)_7CO_2CH_3$, and the mixture of acyclic olefin products comprises $CH_3(CH_2)_7CH=CH(CH_2)_7CH_3$ and $CH_3O_2C(CH_2)_7CH=CH(CH_2)_7CO_2CH_3$.

7. The method of claim 1, wherein the molar ratio of compound III to compound II is about 4 to 1.

8. The method of claim 1, wherein X is Cl, L is COE and R is $CF_3$.

* * * * *